(12) United States Patent
Keller

(10) Patent No.: US 7,776,050 B2
(45) Date of Patent: Aug. 17, 2010

(54) INSERTION INSTRUMENT FOR A PAIR OF SLIDING PROSTHESES

(75) Inventor: Arnold Keller, Kayhude (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 1102 days.

(21) Appl. No.: 10/912,225

(22) Filed: Aug. 6, 2004

(65) Prior Publication Data

US 2005/0033306 A1 Feb. 10, 2005

(30) Foreign Application Priority Data

Aug. 7, 2003 (EP) .................................. 03018049

(51) Int. Cl.
*A61B 17/60* (2006.01)
*A61F 2/00* (2006.01)

(52) U.S. Cl. ....................................................... 606/99

(58) Field of Classification Search ................... 606/88, 606/99; 623/20.14, 20.31
See application file for complete search history.

(56) References Cited

U.S. PATENT DOCUMENTS

| | | | | | |
|---|---|---|---|---|---|
| 4,364,389 A | * | 12/1982 | Keller | .......................... | 606/86 |
| 5,902,339 A | * | 5/1999 | Keller | ...................... | 623/20.31 |
| 6,743,258 B1 | * | 6/2004 | Keller | ...................... | 623/20.14 |

FOREIGN PATENT DOCUMENTS

| DE | 10335410 A1 | * | 2/2005 |
|---|---|---|---|
| EP | 1 099 430 A1 | | 5/2001 |
| EP | 1 321 116 A1 | | 6/2003 |

\* cited by examiner

*Primary Examiner*—Anu Ramana
(74) *Attorney, Agent, or Firm*—Morrison & Foerster LLP

(57) ABSTRACT

An insertion instrument for a pair of sliding prostheses has, on a support plate, two clamps which are arranged at a predetermined spacing from one another and receive the sliding prostheses. The clamps are connected to the support plate via a releasable coupling and may be provided in any position in the lateromedial (LM) direction, i.e. the clamps can adopt different positions in the LM direction. They are clamped securely in the respectively chosen position by a fixing device.

12 Claims, 2 Drawing Sheets

INSERTION INSTRUMENT FOR A PAIR OF SLIDING PROSTHESES

FIELD AND BACKGROUND OF THE INVENTION

As is known, the human knee-joint comprises two pairs of tibio-femoral articular surfaces, namely a medial pair of articular surfaces and a lateral pair of articular surfaces, which are in each case formed by a femoral condyle and by a dish-shaped tibial articular surface interacting with said femoral condyle. It is known (EP-A-1099430) to replace the articular surfaces of the femoral condyles individually by a slide prosthesis and, for this purpose, to use an insertion instrument which guarantees the exact mutual alignment of the prostheses. The prostheses are held on the instrument by means of clamps which are secured on a support plate of the instrument via a releasable coupling. As soon as the prostheses have reached the desired seat in the operation, the coupling is released and the instrument is withdrawn with the support plate from the clamps which remain on the prostheses until the cement used for securing said prostheses has hardened. The releasable coupling consists of a plug on each clamp and of two receiving openings in the support plate, into which openings these plugs can be inserted with an exact fit. They are secured therein by means of screws which remain accessible during the operation so that they can be undone when the instrument is to be removed from the clamps. To be able to insert prostheses at a different predetermined spacing, different support plates are provided in which the receiving openings for the clamp plugs are at a different, predetermined spacing from one another. This has the disadvantage that a large number of different instruments with different support plates have to be kept in stock. Moreover, there are occasions when the operating surgeon wishes to change the spacing of the prostheses, on the insertion instrument being used, during the actual operation. For this reason, another known instrument was created (EP-A-1321116) in which a guide is provided in the support plate for the plugs provided on the clamps, in which guide the plugs and thus the clamps can be moved in the LM direction (LM=lateral-medial) by means of a threaded spindle. This achieved the objective of being able to adjust the spacing during the operation; however, it also had the disadvantage that the clamps are permanently anchored on the support plate by the threaded spindle and that the instrument can be removed from the implanted prostheses only if the clamps themselves are opened, which is not particularly easy.

SUMMARY OF THE INVENTION

Therefore, the object of the invention is to make available an insertion instrument for sliding prostheses which is of the type first mentioned above and which permits different spacings of the clamps and allows them to be separated from the instrument during the operation.

The solution according to the invention lies in the features of the invention as disclosed hereinafter. Accordingly, the coupling between the claims and the support plate is provided in any the clamps and the position in the LM direction, at least on one of the two clamps, so that the clamp in question can be set to a different spacing from the other clamp, and a fixing means is provided for fixing the clamp in the chosen position.

The coupling provided in any position in the LM direction can, like the known solutions, consist of a plug on the clamp and of an elongate hole arranged in the support plate and receiving the plug. The clamp is guided on the support plate in such a way that it is allowed only a lateral movement of adjustment (in the LM direction).

Both clamps are expediently connected to the support plate via in each case a coupling provided in any position in the LM direction and can be fixed in the chosen position. This is intended to ensure that the two clamps can each be arranged symmetrically with respect to the instrument axis.

For fixing the clamps in the chosen position, the invention provides for a fixing yoke whose ends, transverse to the adjustment direction and release direction of the couplings, press on a coupling part connected to the clamps, namely preferably on the coupling plug. The fixing yoke is connected centrally to the support plate by a pressing means, for example a screw, which can be actuated during the operation. In this way, it is possible to release the coupling during the operation and, if appropriate, close it again after changing the spacing of the clamps. It is not necessary for the fixing yoke to act on the coupling part, which is to be held, exactly perpendicular to the adjustment and release directions. However, this is generally advantageous.

The fixing yoke is, like the coupling, expediently provided in any position in the LM direction, in order to be able to secure the clamps at any desired spacing. If one wishes to permit only certain spacings, for example ones which are in accord with certain tibial prosthesis parts (see, for example, EP-A-1099430), the fixing yoke can also be designed such that it can act on the coupling parts of the clamp plugs only at the desired spacings. For example, the yoke can be provided with projections or indents which match recesses or projections on the plugs. It is also possible to provide several exchangeable fixing yokes, of which each one can interact with the associated clamp plugs only at a predetermined clamp spacing and thus acts as spacing gauge. Finally, there is also the possibility of providing a spacing gauge in addition to the fixing yoke provided in any position in the LM direction. The spacing gauge is on the one hand used for fixing on the support plate at a predetermined position. On the other hand, it has recesses or projections interacting with the clamp plugs or parts thereof to define position.

BRIEF DESCRIPTION OF THE DRAWINGS

The invention is explained in greater detail below with reference to the drawing which depicts an advantageous illustrative embodiment and in which.

DETAILED DESCRIPTION OF THE INVENTION

Figure 1:
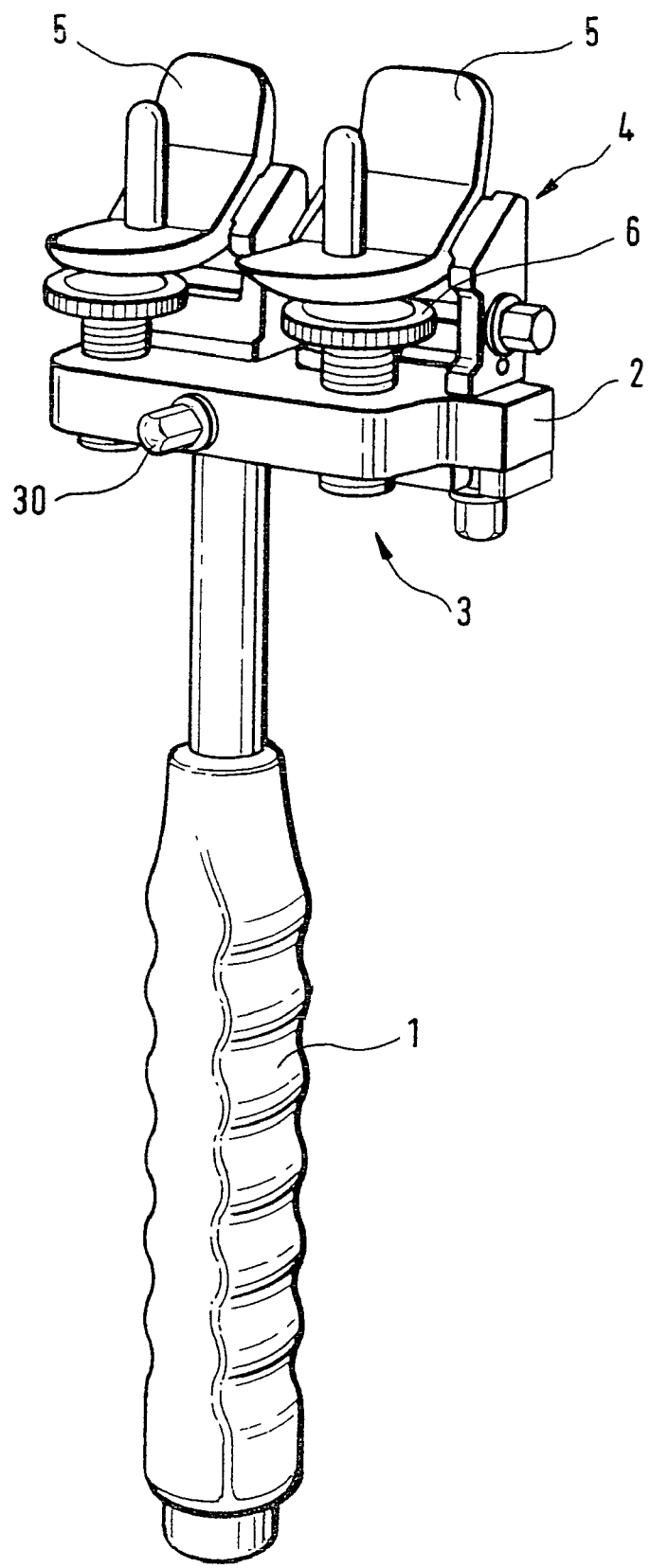
FIG. 1 shows an overall view of the instrument.
Figure 2:
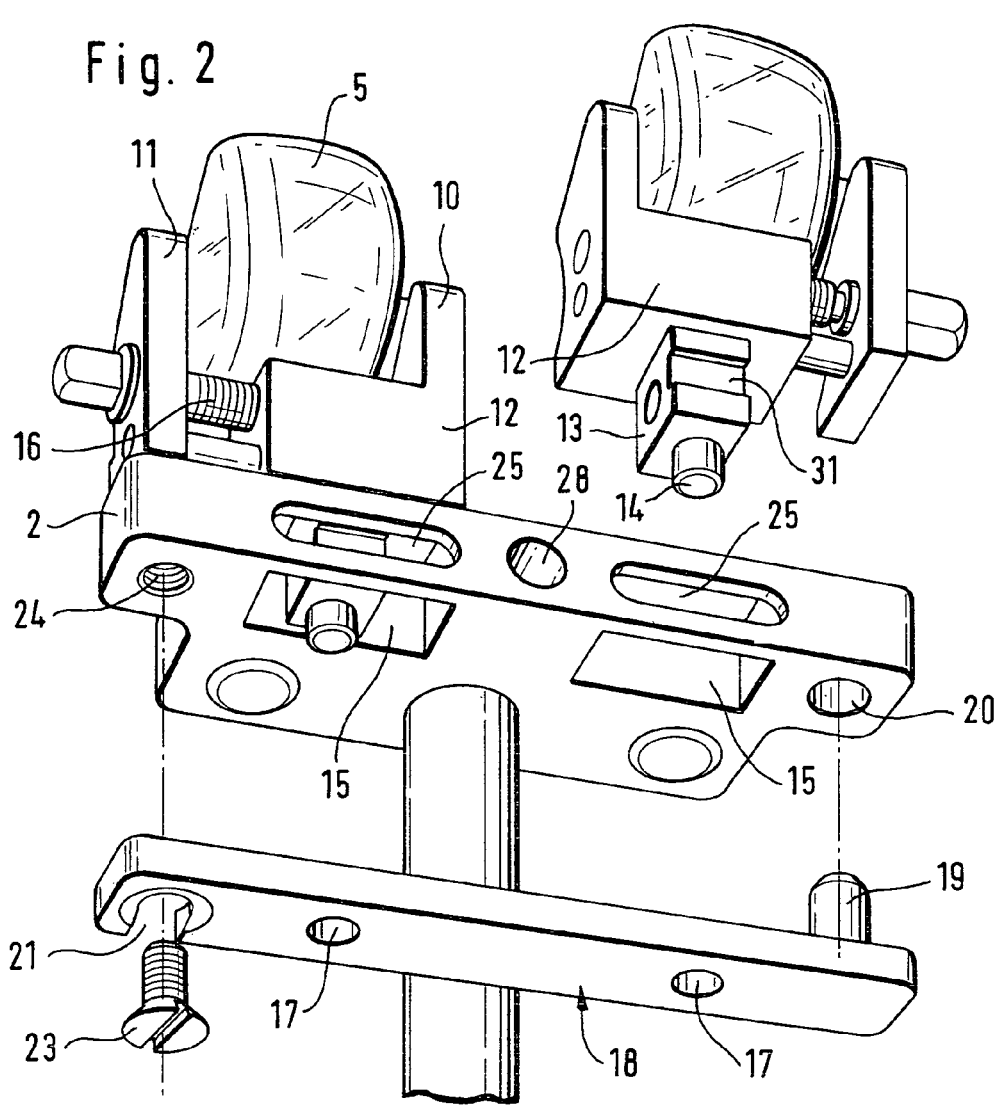
FIG. 2 shows the main parts of the instrument head in a partially exploded view.
Figure 3:
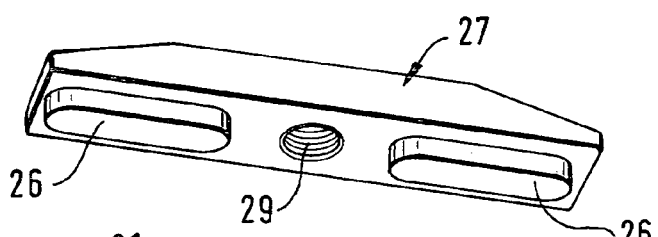
FIG. 3 shows the fixing yoke.

The sliding prostheses 5 are shown obliquely from the dorsal-medial direction in FIG. 1 and obliquely from the ventral direction in FIG. 2. The same direction designations are also applied below to the instrument.

The support plate 2 of the instrument head 3 is secured on a handle with grip 1. The support plate 2 supports two clamps 4 for two sliding prostheses 5, and two slide-surface supports 6.

The slide-surface supports 6 consist of a threaded shaft, mounted in the support plate 2, and of a head with an impact cushion of rigidly elastic plastic. By turning them, they can be adjusted so that their top face bears with a supporting action on the slide surface of the prosthesis part located in the associated clamp 4.

Each clamp 4 comprises a first clamping jaw 10 and a second clamping jaw 11. The foot 12 of the first clamping jaw 10 sits fully on the top face of the support plate 2 and is held by it in a manner which will be explained later. The second clamping jaw 11 is held by the foot 12 of the first clamping jaw 10 so as to be displaceable in parallel. The spacing of the clamping jaws 10, 11 from one another can be adjusted by means of a threaded spindle 16.

Both clamping jaws 10, 11 carry projections which interact with corresponding recesses of the prostheses 5 when the latter are inserted into the clamps 4. In this way, the prostheses are positioned in a defined manner relative to the instrument. Details of this design and of this mode of operation can be found in EP-A-1099430.

Protruding from the underside of each clamp foot 12 there is a plug 13 of rectangular profile which at its lower end carries a small cylindrical attachment 14. The support plate 2 comprises two elongate holes 15 into which a rectangular plug 13 fits exactly in each case. The elongate holes 15 and the plugs 13 form interacting guides in the LM direction of the instrument. Each clamp 4 can therefore adopt different, positions along its line of displacement in the LM direction on the support plate 2. The rectangular plugs 13 and the elongate holes 15 form the abovementioned releasable coupling between the clamps 4 and the support plate 2.

In the assembled state, the plug 13 of rectangular profile is accommodated completely by the associated elongate hole 15. Only the small cylindrical attachment 14 protrudes from the underside of the support plate 2. It interacts with in each case one of two bores 17 in a spacing gauge 18 which can be secured on the underside of the support plate 2. At one end, it has a plug 19 which can be inserted into a matching bore 20 of the support plate, and at the other end it has a laterally open bore 21 which interacts with a screw 23 in a threaded bore 24 of the support plate. Several spacing gauges 18 are made available whose symmetrically arranged bores 17 have a different spacing from one another.

Figure 4:
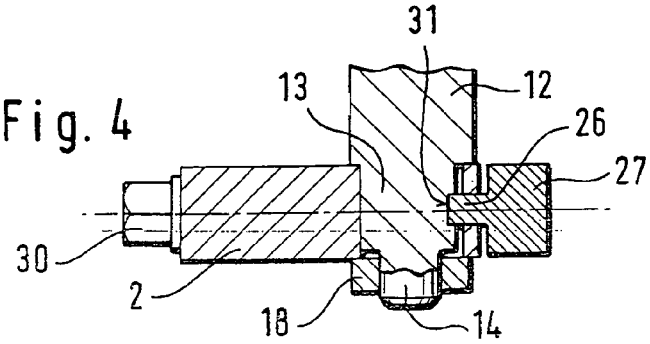
FIG. 4 shows a partial section through the instrument.

On the dorsal face of the support plate 2, the latter is provided with elongate cutouts 25 in the area of the elongate holes 15. These cutouts 25 correspond to projections 26 on a fixing yoke 27 which is applied on the dorsal face of the support plate 2 with projections 26 protruding into the cutouts 25. It is held thereon by means of a threaded screw 30 which passes through the bore 28 of the support plate and engages in the centrally arranged threaded bore 29 of the fixing yoke 27 and whose head is accessible on the ventral face of the support plate 2. When the fixing yoke 27 is drawn onto the rear face of the supporting plate by means of the screw 30, its projections 26 pass through the cutouts 25 and into the elongate holes 15 (see FIG. 4) and press against the rectangular plugs 13 of the clamps 4 present there, by which means these clamps are fixed in their respective position. The rectangular plugs 13 are provided, on the dorsal face, with a transversely extending, shallow groove 31 into which the front of the projections 26 of the fixing yoke 27 engages.

The instrument is used in the following way. Depending on the desired prosthesis spacing, a spacing gauge 18 is selected and is connected to the underside of the support plate 2. The fixing yoke 27 is loosely fastened on the rear face of the support plate 2 by means of the screw 30 so that its projections 26 pass into the cutouts 25 but not yet into the area of the elongate holes 15. The clamps 4 are then fitted so that their rectangular plugs 13 lie in the elongate holes 15 and their small cylindrical attachments 14 lie in the bores 17 of the spacing gauge 18. The fixing yoke 27 is then drawn tight with the screw 30. The clamps are now held secure on the top face of the support plate and at the desired spacing. Thereafter, the prostheses 5 are inserted into the clamps 4. If so desired, this can also be done before the clamps 4 are connected to the support plate 2.

If one wishes to change the spacing of the prostheses, the spacing gauge 18 is removed and the screws 30 are carefully loosened so that the clamps 4 can be moved in the LM direction on the support plate 2. If the projections 26 still engage in the groove 31, they are secured against falling out. Another spacing gauge 18 can now be connected to the support plate, the clamps 4 at the same time being moved so that their cylindrical attachments 14 engage in the newly positioned holes 17 of the spacing gauge 18. Thereafter, the fixing yoke 27 is tightened again.

After the prostheses have attained the desired position on the patient by means of the instrument, the coupling of the instrument between the clamps 4 and the support plate 2 is released. For this purpose, the screw 30 is loosened so that the instrument with the support plate 2 can be withdrawn from the clamps in the caudal direction. This can be done before any cement that is used has hardened.

The invention claimed is:

1. An insertion instrument for a pair of sliding prostheses, comprising:
   a support plate;
   first and second clamps arranged on the support plate at a predetermined spacing from one another and configured to receive the sliding prostheses;
   a first releasable coupling associated with the first clamp and a second releasable coupling associated with the second clamp, the releasable couplings being configured to permit removal of the clamps from the support plate during surgery, the first releasable coupling comprising a first interacting guide configured to provide different predetermined spacings between the clamps by allowing movement of the first clamp along the support plate in a lateromedial (LM) direction of the instrument; and
   a fixing device configured to fix the first clamp in a predetermined position.

2. The instrument as claimed in claim 1, wherein the first interacting guide comprises a plug on the first clamp and an elongate hole in the support plate for receiving the plug.

3. The instrument as claimed in claim 2, wherein the second releasable coupling comprises a second interacting guide configured to allow movement of the second clamp on the support plate in the LM direction.

4. The instrument as claimed in claim 3, wherein the fixing device is formed by a fixing yoke whose ends are disposed transversely to adjustment and release directions of the couplings so as to press on a coupling part connected to the clamps, and the fixing device is coupled to the support plate by a pressing device which can be actuated during surgery.

5. The instrument as claimed in claim 4, wherein the fixing yoke is provided in a predetermined position in the LM direction.

6. The instrument as claimed in claim 5, further comprising an exchangeable spacing gauge.

7. The instrument as claimed in claim 6, wherein the spacing gauge is configured to connect to the support plate.

8. The instrument as claimed in claim 1, wherein the second releasable coupling comprises a second interacting guide configured to allow movement of the second clamp along the support plate in the LM direction.

9. The instrument as claimed in claim 8, wherein the fixing device is formed by a fixing yoke whose ends are disposed transversely to adjustment and release directions of the couplings so as to press on a coupling part connected to the clamps, and the fixing device is coupled to the support plate by a pressing device which can be actuated during surgery.

10. The instrument as claimed in claim 9, wherein the fixing yoke is provided in a predetermined position in the LM direction.

11. The instrument as claimed in claim 10, further comprising an exchangeable spacing gauge.

12. The instrument as claimed in claim 11, wherein the spacing gauge is configured to connect to the support plate.

* * * * *